(12) United States Patent
Hoffmann

(10) Patent No.: US 12,220,700 B2
(45) Date of Patent: Feb. 11, 2025

(54) DEVICE FOR ANALYSING A BIOLOGICAL SAMPLE

(71) Applicant: Robert Bosch GmbH, Stuttgart (DE)

(72) Inventor: Jochen Hoffmann, Renningen (DE)

(73) Assignee: Robert Bosch GmbH, Stuttgart (DE)

( * ) Notice: Subject to any disclaimer, the term of this patent is extended or adjusted under 35 U.S.C. 154(b) by 801 days.

(21) Appl. No.: 17/431,376

(22) PCT Filed: Feb. 12, 2020

(86) PCT No.: PCT/EP2020/053511
§ 371 (c)(1),
(2) Date: Aug. 16, 2021

(87) PCT Pub. No.: WO2020/169422
PCT Pub. Date: Aug. 27, 2020

(65) Prior Publication Data
US 2022/0134335 A1 May 5, 2022

(30) Foreign Application Priority Data
Feb. 19, 2019 (DE) ............... 10 2019 202 174.3

(51) Int. Cl.
*B01L 3/00* (2006.01)
*C12Q 1/6869* (2018.01)
(52) U.S. Cl.
CPC ...... *B01L 3/502715* (2013.01); *C12Q 1/6869* (2013.01); *B01L 2200/04* (2013.01);
(Continued)
(58) Field of Classification Search
CPC .......... B01J 19/0046; B01J 2219/00286; B01J 2219/00353; B01J 2219/00389;
(Continued)

(56) References Cited

U.S. PATENT DOCUMENTS

2003/0118486 A1* 6/2003 Zhou ............... B01J 19/0093
422/400
2003/0150733 A1* 8/2003 Ramsey ............ B01L 3/50273
204/600
(Continued)

FOREIGN PATENT DOCUMENTS

CN 1942590 A 4/2007
CN 105765055 A 7/2016
(Continued)

OTHER PUBLICATIONS

Zhu, Z. et al., "Single-molecule emulsion PCR in microfluidic droplets," Analytical and Bioanalytical Chemistry, 2012, vol. 403, pp. 2127-2143 (17 pages).
(Continued)

*Primary Examiner* — Jennifer Wecker
(74) *Attorney, Agent, or Firm* — Maginot, Moore & Beck LLP

(57) ABSTRACT

A fluidic network for carrying out, in parallel, a plurality of analyses of biological samples is disclosed. The network has a flow cell array with a plurality of reaction chambers. The reaction chambers each have a first channel connection and a second channel connection. The first channel connections are connected to a first supply channel and the second channel connections are connected to a second supply channel. The first supply channel and the second channel connection are interconnected by a circulation line. At least one component is connected to the circulation line so that component test reagents can be introduced into the reaction chambers of the flow cell array.

14 Claims, 5 Drawing Sheets

(52) U.S. Cl.
CPC ............ *B01L 2200/16* (2013.01); *B01L 2300/0663* (2013.01); *B01L 2300/0819* (2013.01); *B01L 2300/0867* (2013.01); *B01L 2300/0877* (2013.01); *B01L 2300/0896* (2013.01)

(58) Field of Classification Search
CPC ............ B01J 2219/00418; B01J 2219/00722; B01L 2200/04; B01L 2200/0668; B01L 2200/16; B01L 2300/0663; B01L 2300/0681; B01L 2300/0819; B01L 2300/0867; B01L 2300/0877; B01L 2300/0896; B01L 3/502715; B01L 3/50273; B01L 3/502738; B01L 3/502769; C12Q 1/6869; C12Q 2535/101; C12Q 2563/155; C12Q 2563/159; C12Q 2565/537; C12Q 2565/629

See application file for complete search history.

(56) References Cited

U.S. PATENT DOCUMENTS

| | | | | |
|---|---|---|---|---|
| 2003/0152994 | A1* | 8/2003 | Woudenberg | G01N 35/08 435/6.12 |
| 2004/0171142 | A1* | 9/2004 | Frank | B82Y 30/00 65/410 |
| 2007/0243634 | A1 | 10/2007 | Pamula et al. | |
| 2011/0244448 | A1* | 10/2011 | Shirai | C12Q 1/66 435/6.1 |
| 2012/0196280 | A1* | 8/2012 | Karlsen | B01L 3/502738 435/6.1 |
| 2016/0038940 | A1* | 2/2016 | Babcock | B81C 1/00206 422/68.1 |
| 2018/0355350 | A1 | 12/2018 | Link et al. | |

FOREIGN PATENT DOCUMENTS

| | | |
|---|---|---|
| WO | 2007/081385 A2 | 7/2007 |
| WO | 2010/100265 A1 | 9/2010 |
| WO | 2011/002957 A2 | 1/2011 |
| WO | 2015/002975 A1 | 1/2015 |

OTHER PUBLICATIONS

International Search Report corresponding to PCT Application No. PCT/EP2020/053511, mailed May 4, 2020 (German and English language document) (6 pages).

Lina et al., "Progress of Application of Microfluidic Chip", Chemical Bulletin, 2010, pp. 892-899, Issue 10, China Academic Journal Electronic Publishing House, DOI: 10.14159/j.cnki.0441-3776.2010.10.016.

* cited by examiner

DEVICE FOR ANALYSING A BIOLOGICAL SAMPLE

This application is a 35 U.S.C. § 371 National Stage Application of PCT/EP2020/053511, filed on Feb. 12, 2020, which claims the benefit of priority to Serial No. DE 10 2019 202 174.3, filed on Feb. 19, 2019 in Germany, the disclosures of which are incorporated herein by reference in their entirety.

BACKGROUND

What is described here is a device for analyzing a biological sample, the device being more particularly a fluidic network for parallel performance of a multiplicity of analyses of biological samples. The biological sample is in particular a sample having nucleic acid sequences contained therein. The analysis which is performed using the device is directed in particular at the identification of a nucleic acid sequence or at establishing whether a certain nucleic acid sequence is contained in a sample (or not). Such analyses are particularly necessary for the decoding of genetic codes (DNA sequencing).

The decoding of the genetic code (DNA sequencing) is a standard method in research and medicine.

One particular form of such analyses is so-called next generation sequencing (NGS). The term "next generation sequencing" refers to a whole range of different methods for sequencing that are all essentially distinguished by the fact that a relatively large quantity of analyses can be performed within a short time (particularly also in parallel) in an automated manner. "Next generation sequencing" methods mainly use sequencing-by-synthesis methods.

In these methods, the DNA molecules to be sequenced are first multiplied (clonally amplified) and bound on a solid phase. The identification of certain nucleic acid sequences is achieved with the aid of labels (fluorescently labeled and terminated nucleotides) which attach to the DNA molecules at sites at which certain patterns exist. When the product strand is synthesized, the incorporation of individual fluorescently labeled nucleotides on the DNA is measured, which ultimately makes it possible to deduce the sequence. The methods performed in these systems are also referred to as sequencing-by-synthesis (SBS).

In SBS, the sequence is generally read by the cyclic performance of the following steps:
1) Exposing (=introduction+incubation) the reaction zone to fluorescently labeled and terminated nucleotides.
2) Incorporating the nucleotides.
3) Washing/flushing the reaction zone.
4) Optically detecting fluorescence events and identifying where the nucleotides were incorporated.
5) Exposing (=introduction+incubation) the reaction zone to a solution for the removal of the terminated nucleotides.
6) Washing/flushing the reaction zone.

A challenge for the miniaturization of such a sequencing method is the multiplicity of wash and flush steps which are performed in order to supply the multiplicity of varying fluids to the reaction zone. Commercial sequencers require, for example, up to 100 mL [milliliters] of wash solution per sequencing procedure.

SUMMARY

What shall be described here is a device which can efficiently perform an analysis of biological samples (more particularly DNA samples) by the approach of sequencing-by-synthesis. Using the described device, it is possible in particular to drastically reduce the volumes of the individual reagents (reagents containing nucleotides, flush solutions, etc.) that are required for a sequencing procedure.

The device described here is a fluidic network for parallel performance of a multiplicity of analyses of biological samples, comprising a flow array having a multiplicity of reaction spaces, wherein the reaction spaces each have a first channel connection and a second channel connection, wherein the first channel connection is connected to a first supply channel and the second channel connection is connected to a second supply channel, wherein the first supply channel and the second channel connection are connected to one another by means of a circulation line, wherein the circulation line has connected thereto at least one component by means of which test reagents are introducible into the reaction spaces of the flow array.

The core of the described fluidic network is the flow array. The flow array contains the reaction spaces in which it is possible to perform the analyses for which the described fluidic network is intended. The flow array preferably has a multiplicity of reaction spaces—for example more than 100 reaction spaces, more than 200 reaction spaces or even more than 1000 reaction spaces.

The fluidic network is in particular a microfluidic network. The term "microfluidic" refers here especially to the size of the microfluidic device. In this connection, the microfluidic device is particularly characterized in that, in the fluidic channels and chambers arranged therein, physical phenomena generally attributed to microtechnology are relevant. These include, for example, capillary effects, effects (particularly mechanical effects) associated with surface tensions of the fluid. These further include effects such as thermophoresis and electrophoresis. In microfluidics, these phenomena are usually dominant over effects such as gravity. The microfluidic device can also be characterized in that it is produced at least in part using a layer-by-layer method and that channels are arranged between layers of the layer structure. The term "microfluidic" can also be characterized by the cross sections within the device that serve for guidance of the fluid. Cross sections in the range from 10 µm [micrometers]×10 µm right up to 800 µm×800 µm are usual for example.

The fluidic network is preferably formed in the manner of a lab-on-a-chip. In this connection, the fluidic network can be for example part of a lab-on-a-chip, for example be arranged in and/or on the chip. Furthermore, the fluidic network can be integrated in and/or on the chip.

The term "channel connection" means connections of the reaction spaces to so-called supply channels that serve as a kind of distributor in order to distribute fluid from the circulation line into the individual reaction spaces of the flow array. In particular, the first channel connections are connected to a common first supply channel and/or the second channel connections are connected to a common second supply channel.

The circulation line serves for the central control of the introduction of reagents into the reaction spaces. Liquid plugs (segments of liquid, separated by a conveyance medium, such as oil for example) in the circulation line can, as a result of conveyance in the circulation line, be introduced into the reaction chambers via the supply channels and the channel connections.

The term "component" means all components which serve for the introduction of reagents into the flow array or for the control of said introduction, for example conveyors, filters, reservoirs, valves It is particularly preferred when the fluidic network is configured for analyzing a biological DNA sample and for identifying nucleic acid sequences in the DNA sample.

The fluidic network is also preferred when the circulation line has connected thereto at least one conveyor by means of which reagents are conveyable into the reaction spaces via the first supply channel and/or via the second supply channel.

The conveyor is, for example, a piston pump or membrane pump. Particularly preferably, the conveyor has a specifically reversible conveying direction in order to allow conveyance in the circulation line in both directions and to hence be able to influence whether and, if so, when and how liquid plugs containing certain reagents pass into the reaction chambers of the flow array.

The fluidic network is further preferred when the circulation line has connected thereto at least one reservoir in which a reagent is provided.

Particularly preferably, the circulation line has connected thereto a multiplicity of such reservoirs. Particularly preferably, there are firstly reservoirs for reagents which play an active role in the analysis process performable using the described fluidic network (so-called reaction reagents). Particularly preferably, there are additionally reservoirs for further fluids which have merely a mechanical or fluid-mechanical effect in the operation of the fluidic network (such as, for example, conveyance medium provided between the plugs). These include, for example, fluids which are substantially inert for the reactions performed in the context of operation of the described fluidic network. Such fluids serve in particular for separation of reaction reagents from one another. Such fluids are oils in particular.

The fluidic network is particularly preferred when the circulation line has connected thereto at least one reservoir in which a displacement medium is provided.

Liquid can be specifically displaced using a displacement medium. In particular, it is possible to displace liquids which interact with other reagents and/or samples in the context of analysis methods performed using the described device. It is thus possible to achieve a separation of reagents from one another and/or of samples and reagents from one another.

The displacement medium can be a mineral oil, silicone oil, a fluorinated oil or derivatives or mixed forms of said oils.

Particularly preferably, such reservoirs are connectable to the circulation line in such a way that they can each be specifically actively connected or deactivated, with the result that fluids can specifically pass into the circulation line from individual reservoirs and are therefore also specifically suppliable to the reaction spaces in the flow array.

The fluidic network is further preferred when at least one reservoir is connectable to the circulation line by means of a valve.

Multiple valves can also be provided in order to (specifically) connect reservoirs. For example, what can be realized are valve arrangements by means of which the circulation line can be connected either past the particular reservoir or through the particular reservoir in order to provide reagents from the particular reservoir into the circulation line and hence also for the processes within the reaction chambers.

The fluidic network is also preferred when the circulation line has arranged therein at least one filter by means of which a reagent moved in the circulation line is filterable.

Such a filter may also be optionally connectable to the circulation line via valves. Said filter serves for purification of the fluids conveyed in the circulation line.

Furthermore, the fluidic network is advantageous when the reaction spaces in the flow array are arranged in (or to form) a two-dimensional matrix. In other words, this means in particular that the reaction spaces are arranged relative to one another in such a way that they form together a (two-dimensional) matrix.

Such an arrangement makes it possible to provide reaction spaces on the flow array in a compact and space-saving manner.

The fluidic network is further preferred when the reaction spaces in the flow array are separated from one another by means of partition webs.

Particularly preferably, the flow array can be realized as a kind of perforated plate in which the individual holes form the reaction chambers and the material remaining therebetween form the partition webs.

The fluidic network is also preferred when the reaction spaces have provided therein retention projections by means of which particles can be held in the reaction spaces.

Furthermore, the fluidic network is preferred when a first side of the flow array has arranged thereon a coupling-in zone for introduction of an excitation by means of an excitation unit and a second side of the flow array has arranged thereon a reading zone for optical reading of the flow array by means of a detection unit. In this connection, the coupling-in zone is generally configured for introduction of an excitation by means of an excitation unit. In this connection, the reading zone is generally configured for optical reading of the flow array by means of a detection unit. There are also optical methods in which excitation light and reading of the emitted fluorescent signals are effected from the same side. If such methods are used, it is also possible that the coupling-in zone and the reading zone are formed together on one side (on the first side or the second side of the flow array.

The first side and the second side (and hence also the coupling-in zone and the reading zone) are arranged on planar sides of the flow array that are opposite (one another) and they are each preferably situated on the side of the first supply channel or the second supply channel that is facing away from the flow array. The excitation unit is preferably configured (e.g., by means of radiation) to excite optical labels in the reaction spaces of the flow array, so that they emit an optical signal. The detection unit (e.g., a camera) is preferably configured to detect such optical signals and to hence also allow an evaluation.

What shall also be described here is a fluidic network, wherein the flow array is realized as an exchangeable insert component. In this connection, the flow array can, for example, be formed in the manner of an exchangeable module. In particular, the flow array is detachably connectable to the rest of the described device (to the rest of the fluidic network). In this connection, it is particularly advantageous when the insert component is formed with a material which differs from at least one material of the rest of the device.

The flow array can in particular be realized as a cartridge which is insertable into the rest of the described device (the described fluidic network) in an exchangeable manner. As a result of the insertion of the flow array, the reaction spaces of the flow array are connected to the supply channels and hence also to the circulation line.

The fluidic network is particularly preferred when a diameter of reaction spaces in the flow array is between 1 nm [nanometer] and 500 μm [micrometers], more preferably between 1 μm and 50 μm.

Reaction spaces in this order of magnitude have been found to be particularly advantageous for the described device (the described fluidic network) and the tests performable therewith.

The core of the described device is the flow array, which can in particular be presented as a miniaturized perforated plate. The individual holes of said perforated plate are the reaction chambers in which the individual identification steps can take place. Preference is given to arranging in each of the reaction chambers various nucleotides on which the DNA molecules to be sequenced have been immobilized, which DNA molecules can pass into the reaction chambers via the supply channels. Furthermore, the DNA sequences to be sequenced can also be produced by a process known in the prior art called BEAMing. The beads formed here, on the surfaces of which a multiplicity of DNA strands of identical sequence have been bound, can, in a next step, be flushed into the perforation array and retained (=fixed) therein. Through the combination of a water-insoluble, immiscible phase (e.g., mineral oil) with the aqueous process liquids, what can be achieved in such a flow array is an advantageous sequencing according to the following basic principle: in a first step, the perforations can be exposed to/filled with the liquid of the particular step, which is done via the supply channels. In the next step, the top and bottom side of the perforation array can be sealed by overcoating and/or undercoating with oil, which can likewise be done via the supply channels.

In this fluidic state (when the reaction chambers are closed), the particular process steps of "sequencing-by-synthesis" can be performed. Prior to performance of the next process step of "sequencing-by-synthesis", the liquids in the reaction chambers of the previous step can, then, be directly displaced by flushing oil through. As an alternative or in addition, use can be made of water-in-oil plugs, thereby making it possible to flush a small amount of wash solution (provided and conveyed as a plug) through the perforations.

What shall also be described here is a method for performing an analysis of a biological sample, comprising the following steps:
a) Providing a fluidic network as claimed in any of the preceding claims.
b) Providing at least one sample in a flow array of the fluidic network.
c) Providing at least two different reagents in the fluidic network, wherein the two different reagents are separated from one another by a displacement medium.
d) Exposing the sample to the at least two different reagents, wherein direct contact between the reagents is prevented by the displacement medium.

In step b), the sample can, for example, be introduced together with the flow array into the fluidic network. This is particularly applicable when the sample is realized in the manner of a cartridge.

The separation of different reagents in step c) is preferably achieved by forming plugs from displacement medium in a circulation line of the described device, which plugs separate different reagents from one another.

The separate exposure of the sample to the different reagents in step d) is preferably achieved by a first reagent being preferably completely displaced from the region of the sample or removed from the sample with the aid of the displacement medium before the sample is exposed to a second reagent.

The described fluidic network and the described method and more particularly the combination of a flow array as sequencing zone, the use of water-in-oil mixtures and the miniaturization of the array are particularly advantageous. This allows in particular one or more of the following advantages:

The described device (the described fluidic network) can reduce all process liquids of a sequencing-by-synthesis method. This is a huge advantage for lab-on-a-chip-based sequencing, in which only limited amounts of reaction solutions are prestorable.

There is a reduction of not only the amounts of required wash reagents, but also of required amounts of reaction solutions containing expensive enzymes. This allows a great reduction in costs.

The flow array makes it possible to place on two different sides of the perforation array the excitation and detection unit required for the optical reading of a sequencing reaction, and this leads to an improved optical efficiency and more arrangement possibilities.

The flow array can be designed as an insert component (such as a DNA microarray), which means freedom in the choice of material and advantages in the process of construction of one of the flow array.

The described fluidic network allows a sample-to-sequence process. This has the enormous potential to identify DNA signatures or even SNPs that cannot be identified by a probe present on the chip. Because of constantly occurring mutations in the target genome, a workflow for sequencing is a key to future-proofing a lab-on-a-chip system.

With the aid of the described fluidic network, there is the possibility of leaving the sequencing reaction to run until gene signatures have been unambiguously determined. It is, for example, also possible to incorporate only a single nucleotide when only the detection of SNPs is concerned.

BRIEF DESCRIPTION OF THE DRAWINGS

The described device will be more particularly elucidated below with reference to the figures. The figures show only a preferred exemplary embodiment, to which the disclosure of the described device is not limited. In the figures.

DETAILED DESCRIPTION

Figure 1:
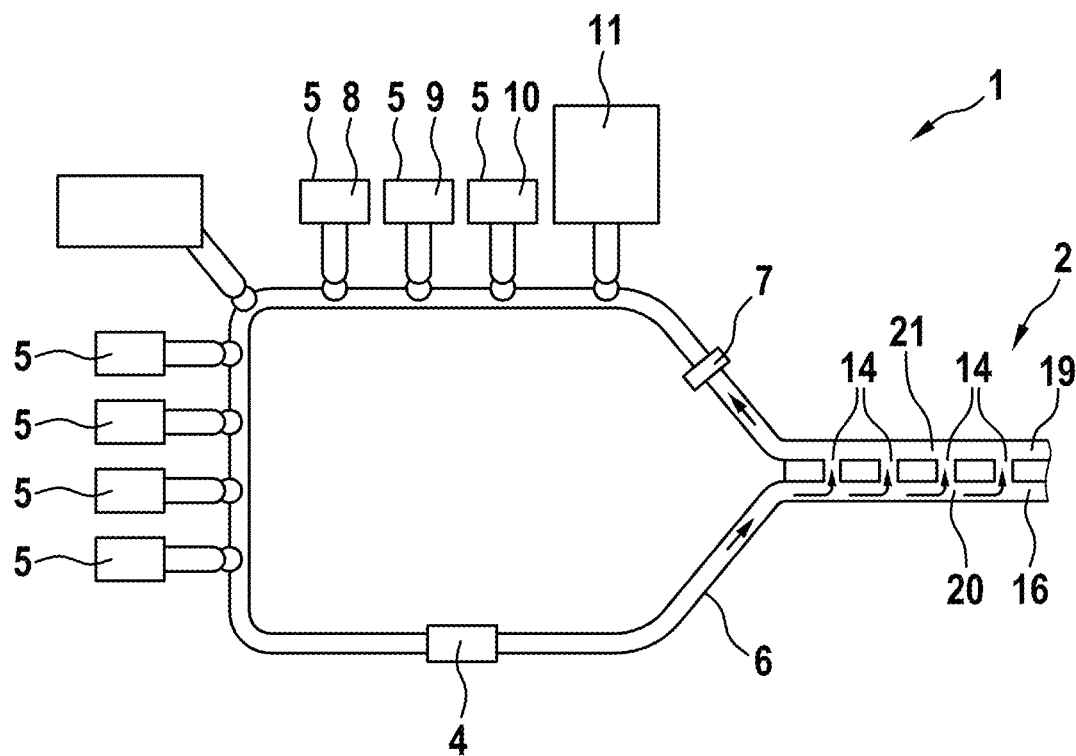
FIG. 1: shows a described fluidic network

FIG. 1 shows a fluidic network 1 for sequencing that is described by way of example. The microfluidic network 1 preferably comprises a circulation line 6 and a flow array 2 having reaction spaces 14. The reaction spaces 14 form flow cells, through which there is parallel flow of a fluid circulating in the circulation line 6. Preferably situated in the reaction spaces are colonies of immobilized DNA molecules. In each individual reaction space 14, a sequencing reaction (=decoding of the sequence of bases) can take place. The reagents intended for this purpose flow, for example, from a first side 22 through a first supply channel 16 into first channel connections 20 of the reaction chambers 14. Preferably, the first side 22 is a bottom side of the flow array 2. This means that the flow array 2 is preferably (geodetically) oriented such that flow therethrough is from the bottom to the top. From the reaction chamber 14, the reagents exit at second channel connections 21 on a second side 24 of the flow array 2 in order to then enter a second supply channel 19. The first supply channel 16 thus preferably forms an inflow channel into the reaction chambers 14. The second supply channel 19 thus preferably forms an outflow channel out of the reaction chambers 14. The first supply channel 16 and the second supply channel 19 are connected to one another via the circulation line 6.

The flow array 2 provides a multiplicity of reaction spaces 14 arranged parallel to one another. Various reservoirs 5 are connected to the microfluidic network 1, separated via valves 3. Said reservoirs 5 hold ready the various reagents intended for a sequencing reaction. For example, for a sequencing-by-synthesis analysis, use is made of labeled nucleotides (e.g., ddNTPs; A=adenine, G=guanine, T=thymine, C=cytosine) which are incorporated by a polymerase (e.g., "Enzyme1") into the nucleic acid sequence to be read. Attached to the incorporated nucleotides is a terminator which prevents the incorporation of a further nucleotide. In a sequencing reaction, said terminator is removed, for example by an "Enzyme2", before the addition of a further nucleotide. Further reagents are the sequencing primer, which defines the starting point of sequencing. Present in further reservoir(s) are wash buffers, by means of which the reaction solutions present in the flow array 2 can be flushed away before a next (reaction) step.

Optionally, the network contains a filter 7. Constituents which were taken up by the wash buffer can be removed using the filter 7. The filter 7 can comprise a dielectrophoretic unit, through which the filtering effect is achieved and with which nucleotides for example can be withdrawn from a solution. This allows a "recovery of wash buffer" for advantageous reduction of wash buffer that is provided. Present in the network is at least one conveyor 4, which can be, for example, a membrane pump or a peristaltic pump. In addition, the fluidic network 1 has a waste reservoir 11 for accommodating reagents that are no longer used. Prestored in a reservoir (not shown) is a displacement medium, which can be used for physical separation of the reagents or for direct displacement of reagents present in the flow array 2 (i.e., a kind of washing support). The displacement medium can be a mineral oil, silicone oil, a fluorinated oil or derivatives or mixed forms of said oils.

Figure 2:
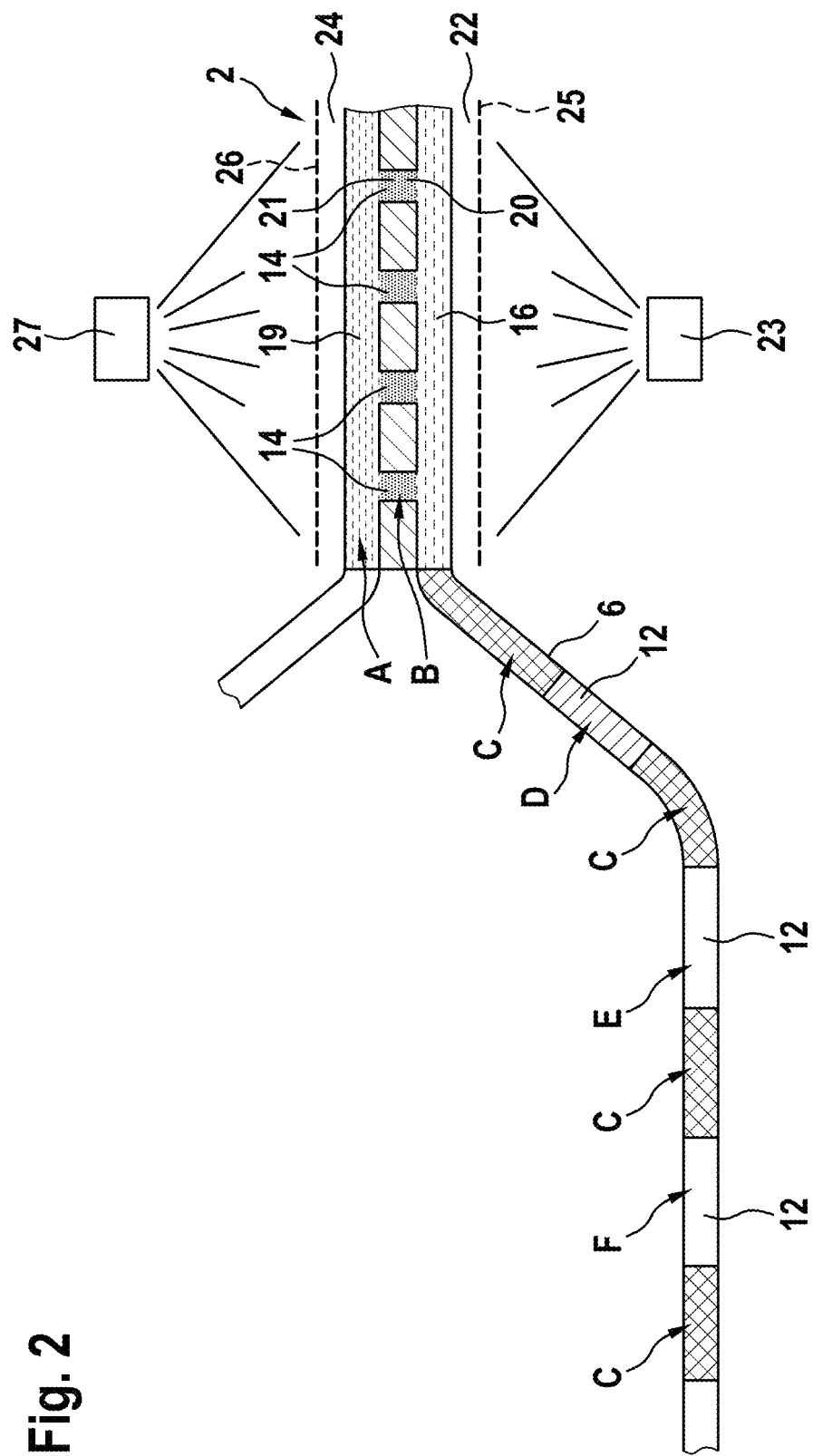
FIG. 2: shows a detail from the fluidic network according to FIG. 1,
FIG. 3: shows a first embodiment of a flow array.

What can be seen in FIG. 2 is an exemplary fluidic detail of sequencing in a described fluidic network 1. FIG. 2 shows primarily the described flow array 2 of the fluidic network 1. What can be identified on the flow array are the reaction chambers 14 having the first channel connections 20 and the second channel connections 21 that have already been described, and also the first supply channel 16 on the first side 22 and the second supply channel 19 on the second side 24 of the flow array. Arranged on the first side 22 is a coupling-in zone 25, at which an excitation unit 23 can deliver an excitation into the reaction spaces 14. Molecules in the reaction spaces 14 can thus be excited so that they emit optical signals. Such optical signals can be detected at a reading zone 26 on the second side 24 using a detection unit 27.

In a section of the circulation line 6 that is depicted in FIG. 2, what can be seen are multiple phases of reagents, which are designated with letters. What can be identified here by way of example are aqueous phases (A, D, E, F), separated from one another by at least one oil phase C (a displacement medium). In the circulation line 6, individual phases (A, D, E, F) form liquid plugs 12, which are each separated from one another by phase boundaries 13 and which can be specifically supplied, with the aid of a conveyor in the circulation line 6 (see FIG. 1), to the flow array 2 or to the reaction spaces 14 contained in the flow array. This is done by conveyance by the conveyor until the respective liquid plugs 12 are in the reaction spaces 14. In order to support the use of the conveyor for accurate conveyance of the liquid plugs 12 into the reaction spaces 14, use can also be made of the excitation unit 23 described above and the detection unit 27 described above.

Before or after the oil phase (or two different phases connected in succession), or in the middle between two oil phases, a wash buffer (generally: an aqueous phase) can also be additionally present. Immobilized on the walls of the cells of the flow array 2 are DNA colonies B in each case (how and where they come from will be explained later). In the figure, the cells (and the construction space therearound) are filled with solution A. In this example, this is, for example, the binding of a sequencing primer. The plug C in contact with B is a combination of wash buffer and displacement medium. With this wash step, the reagents are removed from B from the cells. Now, the multiphase system is transported by the conveyance unit until plug D completely fills the cells of the array. In this continuous example, plug D is a mixture of Enzyme1 and ddNTP "A". When the array is exposed to plug D, the enzyme (a polymerase) incorporates the nucleotide in the case of a "T" present in the strand to be read (because of the base pairing A-T). In the next step, the reaction solution D is washed away by means of the wash buffer C following D, and what takes place is an optical detection of the fluorophores present on the incorporated nucleotides. This is preferably done using the described excitation unit 23 and the described detection unit 27. Now, by means of the conveyor that is not depicted in FIG. 2, the next liquid packet plug E is transported into the cells. Plug E is, for example, Enzyme2, which removes the terminators of the nucleotides. The wash plug C following E is again the combination of wash buffer and displacement medium. Now, by means of the pump unit, plug F is transported into the cells. F is a mixture of Enzyme1 and, for example, ddNTP "C". When the array is exposed to plug F, the enzyme incorporates the nucleotide in the case of a "G" present in the strand to be read (because of the base pairing G-C). This cyclic process is performed until the desired reading length has been reached. By means of an optical check, it is possible to detect the precise positions of the phase boundaries (or in other words: the position of the various liquid plugs).

The detection performed using the detection unit is preferably an optical check. For example, the detection unit is a camera, by means of which the flow array 2 and/or the circulation line 6 can be monitored and by means of which the phase boundaries between the liquid plugs can be identified. For this purpose, the aqueous phases and/or the oil phases can be colored with various dyes or fluorophores (e.g., HEX, FAM dyes; carbon black particles, food dyes, . . . ). By means of this position determination, it is possible to control which solutions are reused and which are fed to a waste container on the circulation line 6 or to a filter on the circulation line 6. An example of the reuse of liquids is, for example, the enzyme mixture Enzyme1+ddNTP "A", "G", "T", "C". These reagents can be recycled into the respective reservoirs in order to be removed therefrom for a renewed incorporation cycle. Similarly, the inert oil plugs can be recycled into the respective reservoir.

Therefore, three approaches for saving buffer volumes are possible with the described fluidic network:
1) Reuse of volumes by recycling into their reservoirs;
2) Use of two-phase mixtures for the reduction of dead volumes and the precise pumping of defined volumes;
3) Filtration options for wash solutions for the reuse of the wash solution.

In what follows, embodiments for providing/immobilizing the DNA colonies to be sequenced (FIG. 2, B) in the colonies are described.

Figure 3:
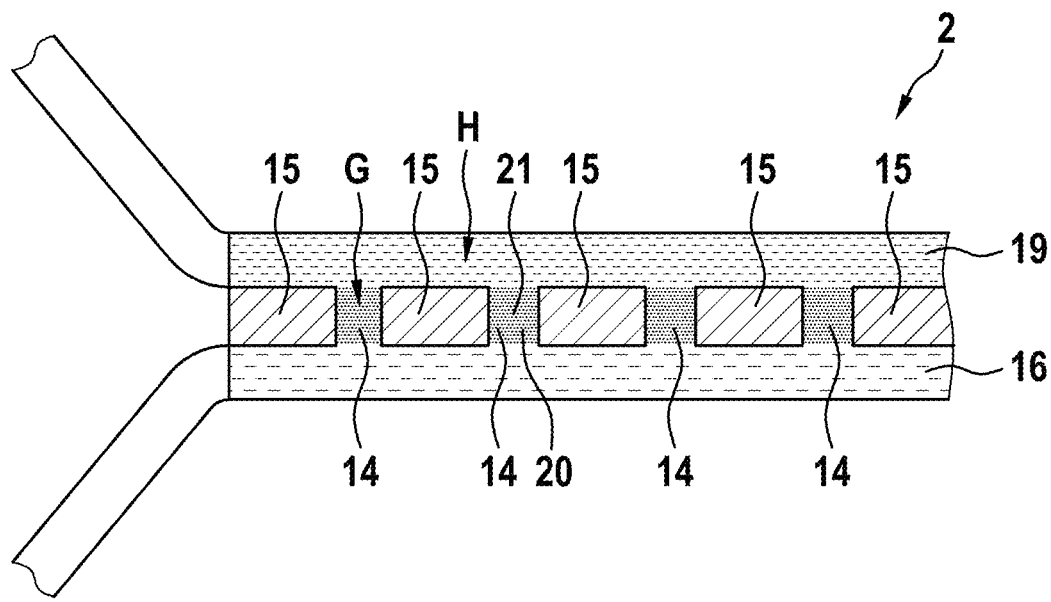

FIG. 3 shows a cross section of the flow array 2. What can be identified are the individual reaction spaces 14, which are separated from one another by partition webs 15 and into which the respective reaction liquids can be introduced through the supply lines 16. The reaction spaces 14 form flow cells of the flow array. Here, the diameter of the reaction spaces 14 or the flow cells is between 1 and 500 μm, preferably between 1 μm and 50 μm. DNA primers can be prestored in the reaction spaces 14 or the flow cells ("targeted sequencing") in order to generate, in the cells, amplification products which are immobilized on the walls of the respective reaction spaces 14/flow cells. Advantageously, a different primer pair is prestored in each of the reaction spaces 14/flow cells in order to be able to read different DNA molecules in the various cells. Such a flow array 2 is filled with a solution which contains at least the DNA molecules to be sequenced and a polymerase. The flow cells/reaction spaces 14 of the flow array 2 are filled with said solution. For the subsequent reaction, the flow array is sealed with the oil "H" such that the first channel connections 20 and the second channel connections (top and bottom side) of the reaction spaces 14 are closed by means of the oil. This state is also shown in FIG. 3. After performance of an amplification reaction (PCR, LAMP, RPA, SDA, . . . ), the resultant DNA colonies "G" are immobilized on the walls of the respective reaction spaces 14. This state is likewise shown in FIG. 3. The successive filling and exchange of solutions in the reaction spaces 14 is carried out as described above, namely by precise conveyance of the fluids in the circulation line.

Figure 4:
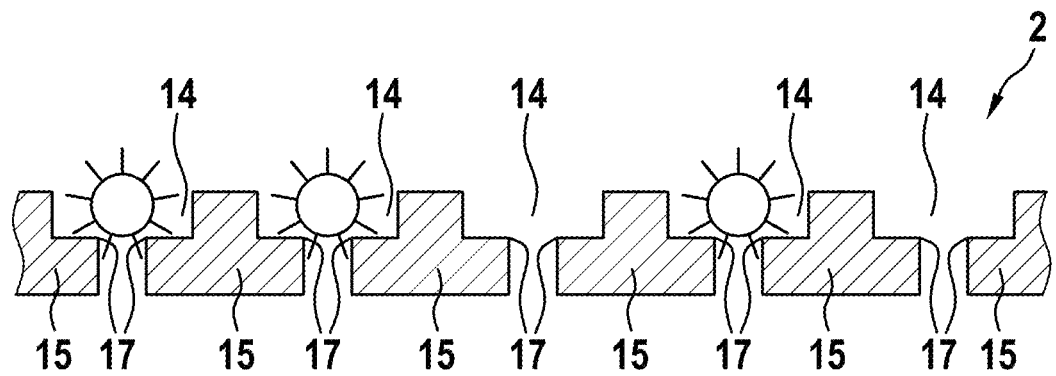
FIG. 4: shows a second embodiment of a flow array.

FIG. 4 shows a further variant as to how the DNA colonies to be sequenced can be present in the cells. What is shown here is a new form of a flow array 2 having reaction spaces 14, FIG. 4 showing only one detail of the flow array 2. In particular, the first supply channel 16 and the second supply channel 19 are not shown here. FIG. 4 focuses on depicting the separating partition webs 15, which separate the individual reaction chambers 14 of the flow array 2 from one another. Here, the reaction spaces 14 are provided with retention projections 17, by means of which particles 18 can be retained. Here, the DNA colonies in the reaction chambers 14 are provided on the particles 18. In the context of a BEAMing method, what are formed are microparticles, on the surface of which the DNA colonies to be sequenced have been immobilized. If a solution containing said particles 18 is flushed through a flow array 2 as shown in FIG. 4, the particles 18 are fixed/positioned by the retention projections 17 present in the flow array 2. A sequencing-capable flow array 2 is thus formed by way of example. The diameter of the openings defined by the retention projections 17 is somewhat smaller than that of the particles. Here, the diameters of the reaction spaces 14 are between 1 nm and 100 μm. Such a flow array containing particles 17 can be sequenced by means of a microfluidic multiphase approach—as described above.

Figure 5:
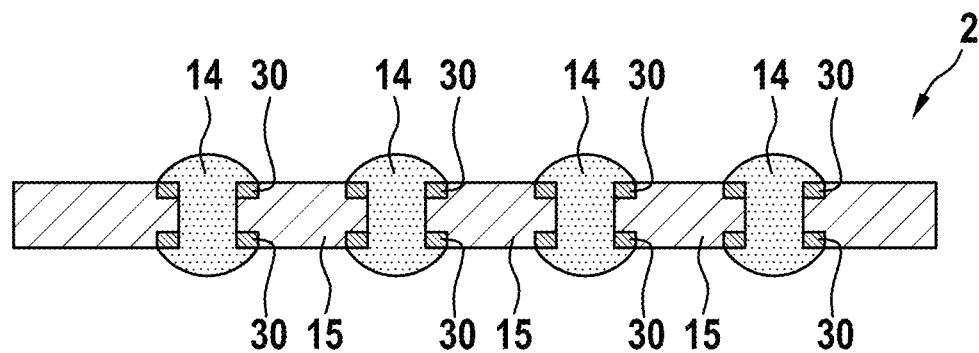
FIG. 5: shows a third embodiment of a flow array.

FIG. 5 shows a further way of generating DNA colonies to be sequenced, in the reaction spaces 14 of a flow array 2. FIG. 5, too, shows the flow array 2 only in highly schematic form. Here, at least the inner walls of the cells and the edge regions on the top and/or bottom side have been hydrophilically coated with a hydrophilic coating 30. The hydrophilic coating 30 on the top and bottom side are shown as black points at the top of FIG. 5. The rest of the array is preferably hydrophobic.

The flow array 2 has (as already described) reaction spaces 14 having a cell diameter of from 1 nm to 100 μm. If such an array is exposed to an aqueous phase, liquid droplets remain in the hydrophilic regions, as shown in FIG. 5. Through this variant, reaction solution can be saved again and the density of cells can be additionally increased. A further advantage is that the DNA colonies can be generated in the context of a digital PCR. Here, the number of DNA molecules to be sequenced is adjusted such that it is comparatively small. When the cells of the array are filled with a solution containing at least the DNA molecules and a polymerase, the molecules are distributed to the cells according to the Poisson distribution (then comes again an amplification reaction, in the context of which the amplification products are immobilized on the walls of the cells).

Figure 6:
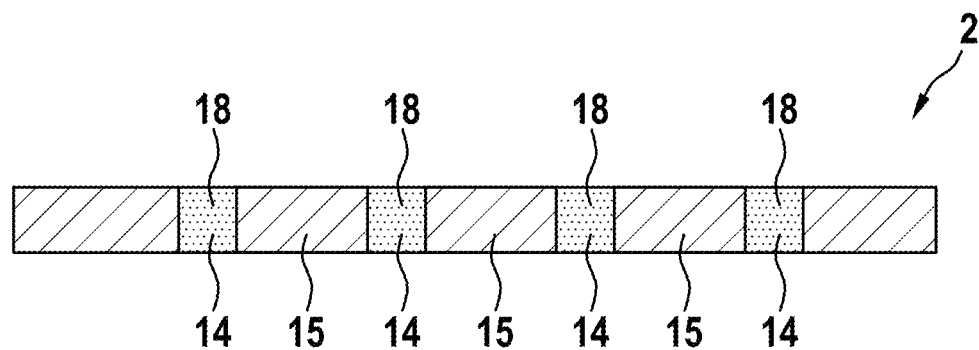
FIG. 6: shows a fourth embodiment of a flow array.

FIG. 6 additionally shows a further embodiment of a flow array. Here, the cells/reaction spaces 14 of the flow array can be shaped with a weblike material 18 or a porous material. This has the advantage that the filling of the cells/reaction spaces 14 is supported by capillary forces, the intended reaction volumes are further reduced and washing by diffusion is made possible.

Figure 7:
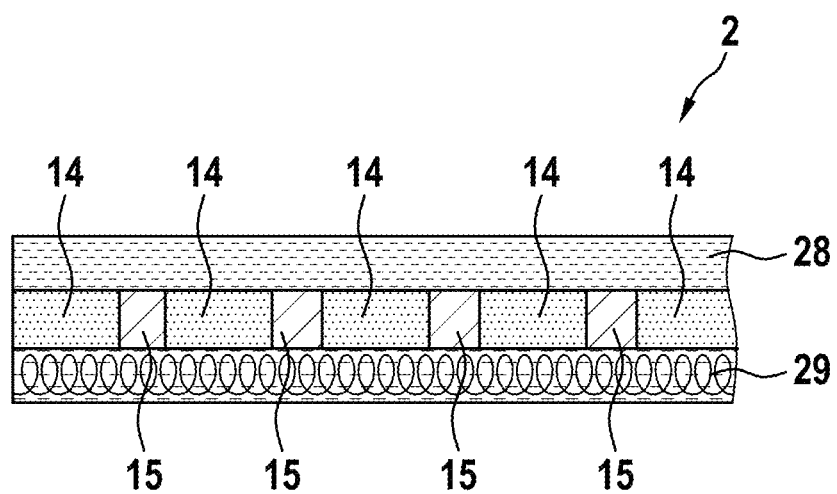
FIG. 7: shows an illustration of operations of a method performable by means of the described device.

FIG. 7 illustrates again the operations of the described method. FIG. 7 shows that one side of the flow array can be closed with an oil phase 28 over the entire sequencing process (or else only for certain steps). Thus, individual aqueous phases 29 of reagents used for a reaction can be flushed across the array on the other side. Here, the washing effect is effected almost exclusively by diffusion. This fluidic principle ("half-closed array") can also be used for a flow array as shown in FIG. 4. Here, the required amounts of wash solution are further reduced.

The method is verifiable by optical inspection of a reaction carrier, specifically the sequencing zone, and analysis of the process liquids used.

The invention claimed is:

1. A fluidic network for parallel performance of a multiplicity of analyses of biological samples, comprising:
a flow array comprising:
a multiplicity of reaction spaces, each of the multiplicity of reaction spaces having a first channel connection and a second channel connection;
a first supply channel connected to each of the multiplicity of reaction spaces by the respective first channel connections; and
a second supply channel connected to each of the multiplicity of reaction spaces by the respective second channel connections such that the multiplicity of reaction spaces are connected to the first and second supply channels in parallel with one another,
a circulation line that connects the first supply channel and the second supply channel to one another outside the flow array; and at least one component connected to the circulation line and configured to introduce test reagents into the reaction spaces of the flow array via the circulation line.

2. The fluidic network as claimed in claim 1, wherein the fluidic network is configured for analyzing a biological DNA sample and for identifying nucleic acid sequences in the DNA sample.

3. The fluidic network as claimed in claim 2, further comprising:
at least one conveyor connected to the circulation line and configured to convey reagents into the reaction spaces via the first supply channel and/or via the second supply channel.

4. The fluidic network as claimed in claim 1, further comprising:
at least one reservoir connected to the circulation line and configured to provide a reagent.

5. The fluidic network as claimed in claim 1, further comprising:
at least one reservoir connected to the circulation line and configured to provide a displacement medium.

6. The fluidic network as claimed in claim 4, further comprising:
a valve configured to connect the at least one reservoir to the circulation line.

7. The fluidic network as claimed in claim 1, further comprising:
at least one filter arranged in the circulation line and configured to filter a reagent moved in the circulation line.

8. The fluidic network as claimed in claim 1, wherein the reaction spaces in the flow array are arranged in a two-dimensional matrix.

9. The fluidic network as claimed in claim 1, wherein the reaction spaces in the flow array are separated from one another by way of partition webs.

10. The fluidic network as claimed in claim 1, wherein each of the reaction spaces include retention projections configured to hold particles in the reaction spaces.

11. The fluidic network as claimed in claim 1, further comprising:
an excitation unit configured to introduce an excitation into the coupling via a coupling-in zone arranged on a first side of the flow array; and
a detection unit configured to optically read the flow array via a reading zone on a second side of the flow array.

12. The fluidic network as claimed in claim 1, wherein the flow array includes an exchangeable insert component.

13. The fluidic network as claimed in claim 1, wherein a diameter of reaction spaces in the flow array is between 1 nm [nanometer] and 100 μm [micrometers].

14. A method for performing an analysis of a biological sample, comprising:
providing a fluidic network as claimed in claim 1;
providing at least one sample in a flow array of the fluidic network;
providing at least two different reagents in the fluidic network, wherein the two different reagents are separated from one another by a displacement medium; and
exposing the sample to the at least two different reagents, wherein direct contact between the reagents is prevented by the displacement medium.

* * * * *